United States Patent [19]
Kellogg

[11] 4,418,945
[45] Dec. 6, 1983

[54] STERILE CONNECTORS

[75] Inventor: Robert M. Kellogg, Washington Crossing, Pa.

[73] Assignee: International Business Machines Corporation, Armonk, N.Y.

[21] Appl. No.: 270,954

[22] Filed: Jun. 8, 1981

[51] Int. Cl.³ ............................................. F16L 55/00
[52] U.S. Cl. ..................................... 285/70; 285/423; 285/DIG. 2; 285/DIG. 16; 604/905
[58] Field of Search ............... 285/3, 70, 423, DIG. 2, 285/73, DIG. 16; 604/408, 409, 410, 204, 905; 251/DIG. 2; 137/67

[56] References Cited

U.S. PATENT DOCUMENTS

| | | | |
|---|---|---|---|
| 3,865,411 | 2/1975 | Marshall et al. | 285/363 |
| 3,909,910 | 10/1975 | Marshall et al. | 29/423 |
| 4,030,494 | 6/1977 | Tenczar | 285/423 |
| 4,149,534 | 4/1979 | Tenczar | 285/423 |
| 4,291,691 | 9/1981 | Cabal et al. | 604/905 |

FOREIGN PATENT DOCUMENTS 2256149  5/1974  Fed. Rep. of Germany ... 251/DIG. 2

Primary Examiner—Dave W. Arola
Attorney, Agent, or Firm—Thomas J. Kilgannon

[57] ABSTRACT

Sterile connectors which utilize tabs or strips, portions of which can be withdrawn from apertures which are to be interconnected in sterile fashion are disclosed. The connectors disclosed are utilized in conditions of differential pressure between the inside of conduits to which the connectors are coupled and the surrounding ambient. Contamination resulting from air flow due to the pressure differential is prevented by encasing the tab or strip in a sleeve or extension which isolates the strip or tab from the surrounding ambient. When a pair of sterile connectors is mated, deformable washers are brought into contact and the tabs or strips are pulled through channels in the washers into the sleeves or extensions while portions of the washers remain in contact forming an hermetic seal.

29 Claims, 13 Drawing Figures

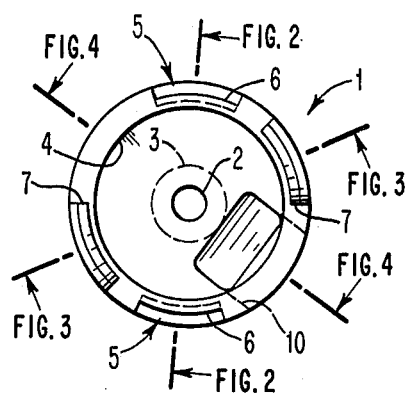
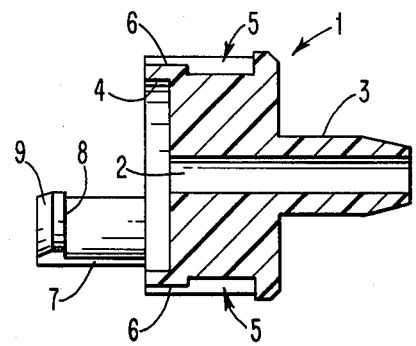
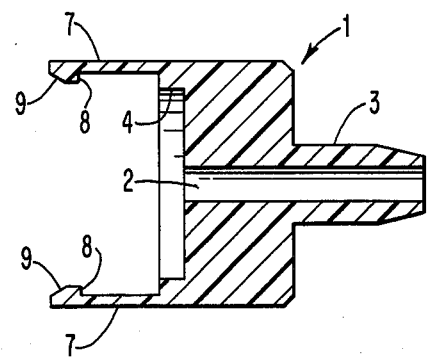
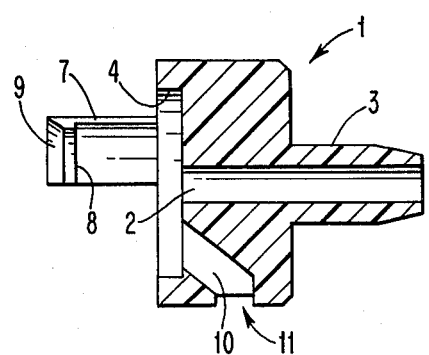

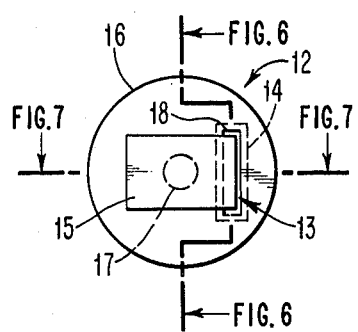
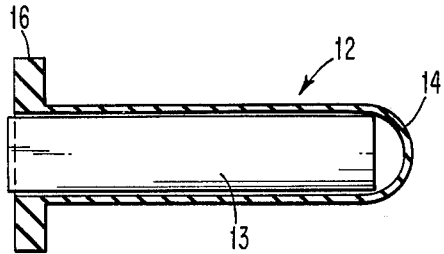
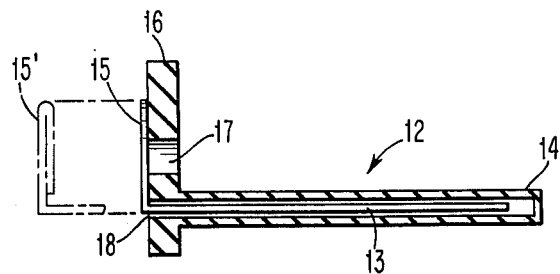
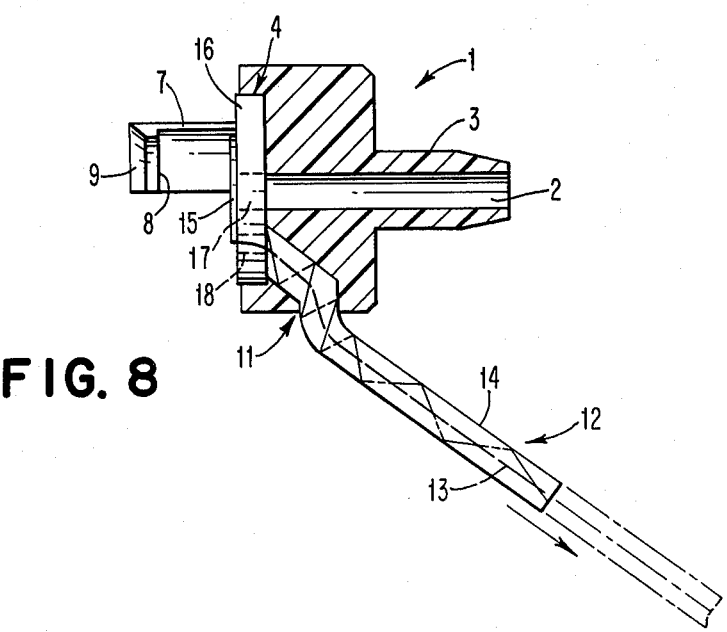

STERILE CONNECTORS

DESCRIPTION

1. Technical Field

This invention relates to sterile connectors and more particularly relates to apparatus which permits the interconnection of two conduits adapted for carrying fluids in a sterile manner where there is a differential pressure between the inside and outside of the conduits. Still more particularly, it relates to sterile connectors which utilize a deformable seal or washer disposed about the terminal end of a conduit and a continuous, removable, yieldable strip material a portion of which is removably adhered to the washer and overlies the end of the conduit. Another portion of the strip extends from the bottom of the washer through a passage in the washer and extends radially from the edge of the washer to form a free end. The free end has an extension or sleeve surrounding it, one end of which is connected to the passage. The sleeve isolates the strip from atmospheric pressure when a force is applied to the free end and to the sleeve to withdraw the strip material and expose the end of the conduit.

2. Background Art

U.S. Pat. No. 3,865,411 filed Mar. 29, 1973 shows a strip element having a U-shape which is disposed over a hole in a flexible washer which is removably adhered to the washer in such a way that when the strip is peeled away, the hole in the washer which is coextensive with a hole in an adjacent conduit is exposed.

U.S. Pat. No. 3,909,910 filed Aug. 13, 1974 relates to a method of joining the ends of two conduits together in a sterile manner and utilizes the apparatus of the above mentioned U.S. Pat. No. 3,865,411.

While the apparatus shown in the above mentioned patents fulfills its desired function where there is no pressure differential between the conduit being uncovered and the surrounding ambient, it leaves something to be desired when there is a pressure differential between the conduit being uncovered and the surrounding ambient. For example, where the pressure in the conduit is lower than that of the surrounding ambient, when the U-shaped strips of the patents are being removed, it is possible that contaminated air will be drawn across the surface of the deformable gasket or washer contaminating either the atmosphere within the conduit or the aperture thereby defeating the purpose for which the apparatus is intended.

From all the foregoing, it should be clear that while the general problem of providing for sterile connectors between conduits has been addressed, the specific problem of providing sterile connections when there is a difference in pressure between the inside of a conduit and the surrounding ambient has not been adequately addressed. In the prior art, making sterile connections in the differential pressure environment has either not been addressed at all or very complex, uneconomical structures have been provided to achieve this end.

It is, therefore, a principal object of this invention to provide a sterile connector which can be utilized when a differential pressure exists between the inside of a conduit and the surrounding ambient.

It is another object of the present invention to provide a sterile connector which is simple in construction, easy to fabricate, simple to use and disposable.

It is another object of the present invention to provide a sterile connector which has enhanced sterility characteristics.

BRIEF SUMMARY OF THE INVENTION

The present invention relates to sterile connectors which utilize tabs or strips portions of which can be withdrawn from apertures which are to be interconnected in a sterile fashion. Because the ambient conditions in which such sterile connectors are to be utilized are not uniform, differences in pressure handle a conduit relative to the pressure of the surrounding ambient can cause undesired airflow which either contaminates the atmosphere within the conduit or contaminates the fluid which is to be kept sterile. The invention of the present application prevents such contamination by encasing the tab or strip in a sleeve or extension thereby isolating the strip or tab from the surrounding ambient. Thus, the sterile connector of the present invention includes a resilient, deformable seal or washer disposed about the terminal end of a conduit. It also includes a continuous, removable, yieldable strip material or tab, a portion of which is removably adhered to the washer or seal and overlies an aperture in the washer which is coaxial with the end of the conduit. Another portion or free end of the strip or tab extends from the bottom of the washer or seal through a channel in the washer and radially from the edge of the washer. Finally, the sterile connector includes means surrounding the free end connected to the channel for isolating the strip from atmospheric pressure when a force is applied to the free end and the isolating means to withdraw the strip material and expose the aperture in the washer. These elements are all held within a rigid body portion which is adapted to mate and lock with another body portion to form a sterile connection.

These and other objects, features and advantages will be more apparent from the following more particular description of the preferred embodiment.

BRIEF DESCRIPTION OF THE DRAWINGS

FIG. 1 is an end view of the body portion of the sterile connector of the present invention showing lines 2—2, 3—3, 4—4 along which the cross-sectional views shown in FIGS. 2, 3, 4, respectively, are taken.

FIG. 2 is a cross-sectional view of the body portion of the sterile connector of FIG. 1 taken along lines 2—2 thereof.

FIG. 3 is a cross-sectional view of the body portion of the sterile connector of FIG. 1 taken along lines 3—3 thereof.

FIG. 4 is a cross-sectional view of the body portion of the sterile connector of FIG. 1 taken along line 4—4 thereof.

FIG. 5 is an end view of the apertured, flexible washer or seal assembly having an elastic extension extending from it. A flexible strip or tab held within the elastic extension or sleeve has an end portion which is adapted to adhesively cover the aperture in the seal assembly providing a sterile region underneath the end portion. The seal assembly and flexible strip or tab in combination with the body portion shown in FIGS. 1–4 form the major elements of the sterile connector of the present invention.

FIG. 6 is a cross-sectional view of the deformable seal or washer and sleeve or extension taken along line 6—6 of FIG. 5 which also shows the positioning of the tab within the sleeve or extension.

FIG. 7 is a cross-sectional view of the deformable seal or washer and elastic sleeve or extension taken along lines 7—7 of FIG. 5 which also shows the positioning of the tab within the sleeve or extension and the positioning of the end portion of the tab over the aperture in the seal or washer.

FIG. 8 is a cross-sectional view of the body portion of the sterile connector similar to that shown in FIG. 4 which also shows the flexible seal assembly assembled with said body portion. A dashed line portion shows the extent to which the sleeve or extension may be stretched when it and the tab are grasped between thumb and forefinger to pull the end portion from over the aperture in the seal or washer. A zigzag line within the extension shows how the tab crinkles up within the extension when the latter is released and allowed to return to its original position.

DESCRIPTION OF PREFERRED EMBODIMENTS

Figure 9:
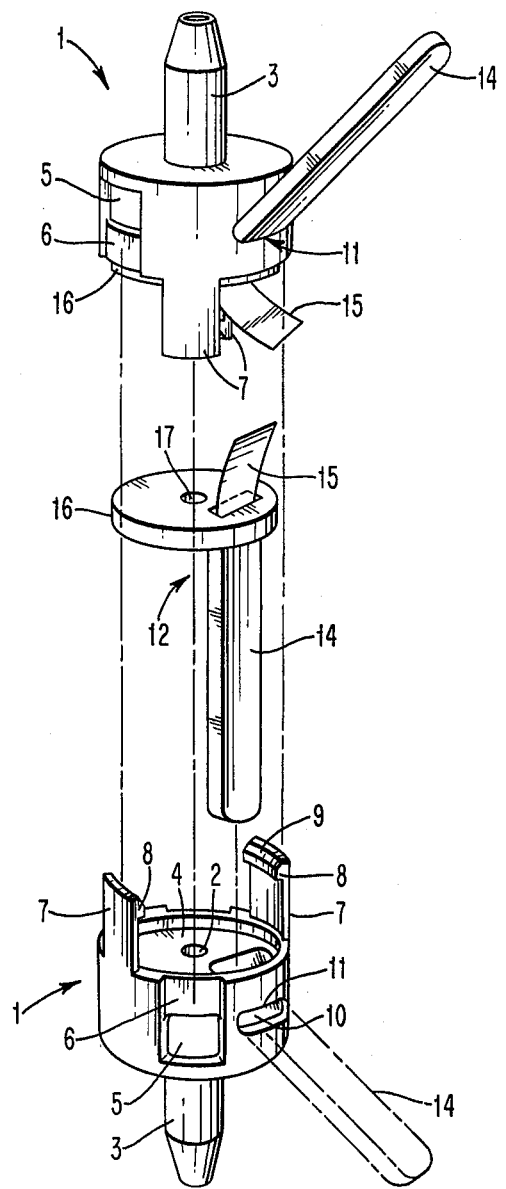
FIG. 9 shows an exploded, perspective view of a pair of sterile connector body portions, one of which is shown fully assembled with the seal assembly and the other of which is shown with the seal assembly removed and with a sleeve or extension in phantom within a body portion.

Referring now to FIGS. 1-4 and more particularly to FIG. 1, there is shown therein an end view of the body portion of the sterile connector of the present invention showing lines 2—2, 3—3, 4—4, along which the cross-sectional views shown in FIGS. 2, 3, 4, respectively, are taken. In FIG. 1, body portion 1 has a circular configuration and may be made of plastic or other material which is compatible with biological fluids. Body portion 1 includes an aperture 2 which extends lengthwise of body portion 1 and through a nipple 3 which extends from body portion 1. A seat 4 is recessed into body portion 1 and, as will be shown hereafter in more detail, is adapted to receive an apertured washer or seal assembly. A pair of slots 5 containing ridges 6 is disposed on the periphery of body portion 1 in diametrically opposing relationship. Slots 5, as will be shown hereinafter in more detail, are adapted to form part of the mechanism which locks a pair of body portions 1 together in tight fitting engagement. The configurations of nipple 3, seat 4, slots 5 and ridges 6 are clearly shown in the cross-sectional view of body portion 1 in FIG. 2.

FIG. 2 shows a flexible tang-like arrangement 7 extending from body portion 1. Tang-like arrangement 7 has a raised lip 8 at its end. Lip 8 has a beveled portion 9 which is adapted to slidably engage a slot 5 in a mating body portion 1 and be held in tight fitting engagement when lip 8 slides over ridge 6. Each body portion 1 has at least a pair of tang-like arrangements 7 as clearly shown in the cross-sectional view of FIG. 3.

FIG. 4 which is a cross-sectional view taken along lines 4—4 of FIG. 1 shows a channel 10 which extends obliquely from the bottom of seat 4 into body portion 1 until it appears as an aperture 11 on the periphery of body portion 1. As will be shown in more detail hereinafter, seat 4 and channel 10 are adapted to receive a flexible washer or seal assembly.

Referring now to FIGS. 5, 6 and 7 which show an end view, a cross-sectional view taken along lines 6—6 of FIG. 5 and a cross-sectional view taken along lines 7—7 of FIG. 5, respectively, of an apertured, flexible washer or seal assembly 12. Each of these views shows a flexible strip or tab 13 disposed within an elastic extension or sleeve 14 and, as shown in FIGS. 5, 7, flexible strip or tab 13 has an end portion 15 which extends at a right angle from the remainder of strip 13 and is adapted to be positioned in adhesively engaging relationship with the surface of a washer or seal 16 and over an aperture 17 in washer or seal 16. Washer or seal 16 and elastic extension or sleeve 14 which make up seal assembly 12 may be made of latex rubber or other elastic material which is compatible with biological fluids like blood. Flexible strip or tab 13 may be made of a plastic such as "Teflon" and an adhesive such as a two part contact adhesive may be used to coat end portion 15 to stick it to the surface of washer or seal 16. While FIG. 7, for example, shows elastic extension or sleeve 14 and washer or seal 16 as a single structural unit, it should be appreciated that these elements can be formed separately and joined by adhesively fixing or heat-sealing sleeve 14 about a passage 18 in washer 16.

In addition, it should be appreciated that end portion 15 can have a different configuration. For example, end portion 15' shown in FIG. 7, may have a U-shaped configuration similar to that shown in U.S. Pat. No. 3,865,411 and is arranged to cover aperture 17 just like end portion 15. To the extent, end portion 15' is not specifically discussed hereinafter, any place end portion 15 is discussed, end portion 15' may be used without departing from the spirit of the present invention.

Considering now FIG. 8, there is shown a cross-sectional view of body portion 1 of the sterile connector of the present invention which is similar to the view shown in FIG. 4. FIG. 8 also shows the deformable seal or washer 16 and elastic extension 14 and tab 13 of FIG. 7 assembled with body portion 1. Thus, in FIG. 8, washer or seal 16 of seal assembly 12 is positioned in seat 4 and elastic extension or sleeve 14 is positioned in channel 10 in such a way that sleeve 14 extends from aperture 11 in the periphery of body portion 1. Apertures 2 and 17 are in registry and end portion 15 of flexible strip or tab 13 is shown disposed over aperture 17. A dashed line portion in FIG. 8 shows the extent to which sleeve or extension 14 may be stretched when it and tab 13 are grasped between thumb and forefinger to pull tab 13 and remove end portion 15 from over aperture 17. A zigzag line within extension or sleeve 14 shows how tab 13 crinkles up within extension 14 when the latter is released and allowed to return to its original position.

FIG. 9 shows an exploded, perspective view of a pair of sterile connector body portions 1, one of which is shown fully assembled with a seal assembly 12 and the other of which is shown with a seal assembly 12 removed and with a sleeve or extension 14 positioned in phantom within a body portion 1. In FIG. 9, a seal assembly 12 is shown assembled with the uppermost of body portions 1 so that elastic extension or sleeve 14 extends from the periphery of body portion 1. It should be noted that the thickness of deformable washer or seal 16 is greater than the depth of seat 4 causing washer 16 to extend slightly from body portion 1. While end portion 15 has previously been indicated as being positioned over aperture 17 in an adhesively engaging relationship, it has not been so shown in FIG. 9 so that the relationship of the various elements can be clearly seen. In any event, in assembled form, an end portion 15 would be adhesively disposed over an aperture 17 in washer 16. The apertured, flexible washer or seal assembly 12 shown exploded outside the lowermost of body portions 1 is assembled by introducing sleeve or extension 14 into channel 10 and pulling it through aperture 11 in lowermost body portion 1. Extension 14 shown in phantom in FIG. 9 shows the juxtaposition of extension 14 relative to lowermost body portion 1. Deformable washer 16, of course, fits within seat 4 and, like washer 16 disposed in uppermost body portion 1 extends slightly above the surface of its associated body portion 1.

In FIG. 9, tangs 7 and slots 5 are displaced apart from each other on body portions 1 by approximately 45 degrees. To assemble body portions 1, tangs 7 of uppermost body portion 1 are moved to engage slots 5 of lowermost body portion. At the same time, tangs 7 of lowermost body portion 1 engage slots 5 of uppermost body portion 1. When body portions 1 are pushed together, beveled portions 9 of raised lips 8 of tangs 7 slide into slots 5 as far as the compression of deformable washers or seals 16 permits. When the pressure is released, deformable washers 16 force raised lips 8 back against ridges 6 locking body portions 1 of FIG. 9 together in airtight, engaging relationship. When portions 1 are so engaged, a sterile connection between apertures 17 can be made by grasping elastic extensions or sleeves 14 and flexible strips or tabs 13 disposed within them between thumb and forefinger and pulling so that end portions 15 are removed from over apertures 17 in washers 16. When body portions 1 are mated as just described, the outsides of end portions 15 are in registry. In this manner, a contaminated surface faces a contaminated surface. By then grasping sleeves 14 simultaneously and pulling, end portions 15 slide away together permitting uncontaminated portions around apertures 17 to mate in a sterile fashion.

At this point, it should be appreciated that air cannot flow because of differential pressure between the ambient air and the inside of aperture 2 because deformable washers or seals 16 are butted together in a compressed, hermetically sealed relationship. The withdrawal of end portions 15 is achieved without breaking the hermetic seal because there is no separation of portions of washers 16 between the edge of passages 18 and the periphery of washers 16.

To the extent that elastic extensions or sleeves 14 must be arranged on the same side of body portions 1 to insure an uncontaminated connection, a tang 7 and its associated slot 5 on another body portion 1 can be sized differently from the other tang 7, slot 5 combination.

Figure 10:
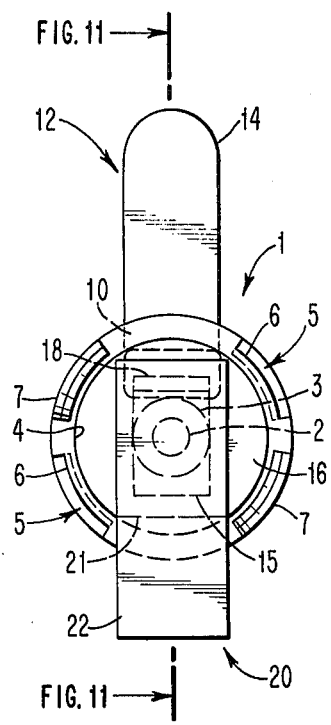
FIG. 10 is an end view of a body portion of the sterile connector of the present invention showing the assembled body portion and seal assembly with a diaphragm disposed over the end portion of the tab which covers the aperture in the seal assembly.

Referring now to FIG. 10, there is shown an end view of a body portion of the sterile connector of the present invention showing an assembled body portion and seal assembly with a diaphragm disposed over the end portion of the tab which covers the aperture in the seal assembly. Elements in FIG. 10 which are the same as those in previous figures are identified with the same reference characters. In addition to body portion 1 and apertured flexible washer or seal assembly 12, FIG. 10 shows a diaphragm 20 disposed over end portion 15 and passage 18. Diaphragm 20 is made from the same material as flexible strip or tab 13 and is disposed in adhesively engaging relationship with the surface of washer or seal 16 by means of an adhesive which is disposed only on the periphery of diphragm 20 where it touches the surface of washer or seal 16.

Figure 11:
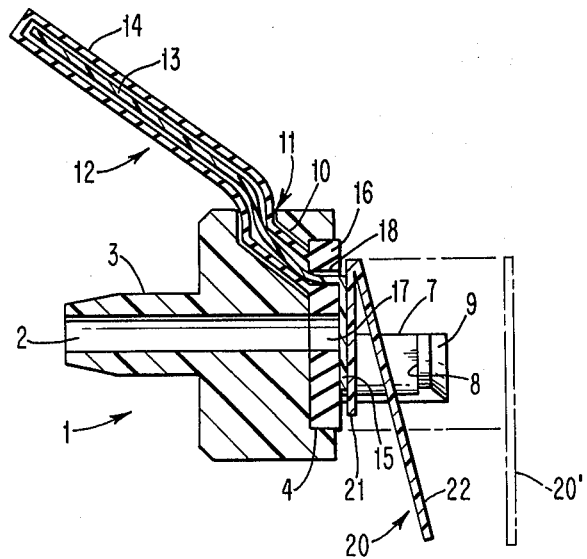
FIG. 11 is a cross-sectional view taken along lines 11—11 of FIG. 10 showing the diaphragm in the form of a generally U-shaped member disposed over the end portion of the tab which covers the aperture in the seal assembly. An alternative diaphragm is also shown.

The juxtaposition of the various elements is better seen in FIG. 11 which is a cross-sectional view taken along lines 11—11 of FIG. 10 and shows diaphragm 20 in the form of a generally U-shaped member disposed over the end portion of the tab which covers the aperture in the seal assembly. In FIG. 11, diaphragm 20 includes a sterile portion 21 and a free end 22. While sterile portion 21 is shown in FIG. 11 as being out of contact with the surface of washer 16, for purposes of clarity, it should be appreciated that the overhanging portion of sterile portion 21 facing the surface of washer 16 is, in practice, adhesively connected to portions of the surface of washer 16. Diaphragm 20 having a generally U-shaped configuration as shown in FIGS. 10,11 is identical with that shown in U.S. Pat. No. 3,865,411 which was alluded to hereinabove in the Background Art Section.

FIG. 11 shows another diaphragm 20' which may be substituted directly for diaphragm 20 having the U-shaped configuration. Diaphragm 20' would be disposed over end portion 15 in exactly the same manner as sterile portion 21 and adhesively connected to surface portions of washer 16 in the same manner as sterile portion 21.

Figure 12:
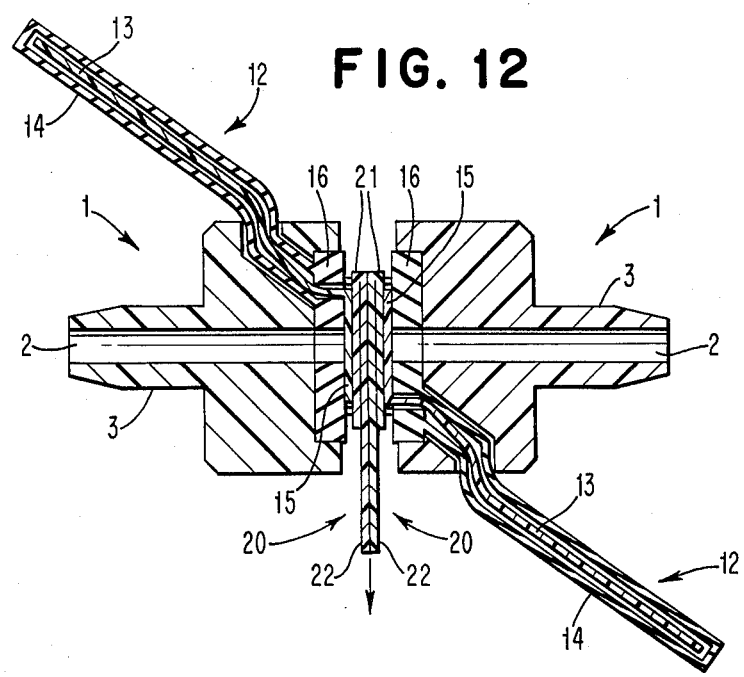
FIG. 12 is a cross-sectional view similar to that shown in FIG. 11 of a pair of sterile connector body portions, seal assemblies, tabs and diaphragms which shows the relationship of these elements as they appear assembled and prior to the removal of diaphragms and tabs.

Referring now to FIG. 12, there is shown therein a cross-sectional view similar to that shown in FIG. 11 of a pair of sterile connector body portions 1, seal assemblies 12, tabs 13 and diaphragms 20 which shows the relationship of these elements as they appear assembled and prior to the removal of diaphragms 20 and tabs 13. To the extent that the dimensions of tabs 13 and diaphragm 20 have been exaggerated for purposes of clarity, body portions 1 in FIG. 12 are spaced further apart than they would be in actual practice. In use, surface portions of deformable washers 16 would touch each other everywhere except where free end portions 22 are interposed.

In use, body portions 1 are locked together by means of tangs 7 in slots 5 as previously described in connection with FIG. 9. When locked together, the sterile connector has the configuration shown in FIG. 12 wherein extensions 14 extend from opposite sides of the sterile connector while diaphragms 20 extend from the same side of the sterile connector. Under such circumstances, a contaminated portion of one free end 22 faces a contaminated portion of another free end 22. To achieve a sterile connection between body portions 1, free ends 22 of diaphragms 20 are both pulled simultaneously in the direction shown by the arrows in FIG. 12 so that sterile portions 21 of both diaphrams 20 are peeled away from their position around end portions 15. When diaphragms 20 have been completely withdrawn, sterile surfaces of end portions 15 face each other. This intermediate situation is shown in cross-section in FIG. 13. To form the sterile connection, extensions 14 and tabs 13 are withdrawn either simultaneously or sequentially in the same manner as described hereinabove in connection with the description of FIG. 9. To the extent that surface portions of deformable washers 16 are now in compressed contact at their peripheries, no airflow due to a pressure differential can occur across the surface of washers 16 and the withdrawal of end portions 15 into sleeve 14 occurs without disturbing the seal at the peripheries of washers 16.

Figure 13:
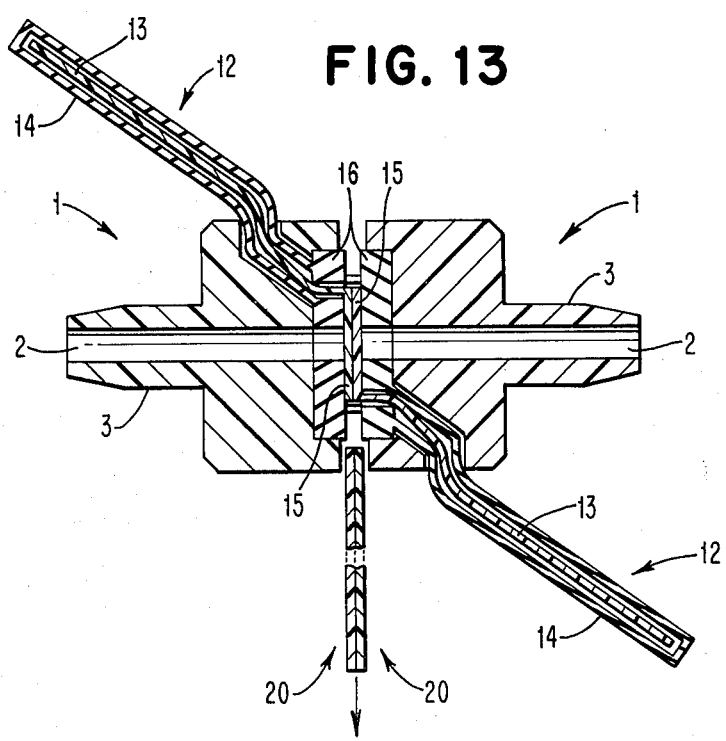
FIG. 13 is a cross-sectional view similar to that shown in FIG. 12 after the removal of the diaphragms and prior to the removal of the portions of the tabs or strips from over their associated apertures.

As indicated hereinabove in connection with FIG. 11, a diaphragm 20' may be substituted in FIGS. 12 and 13 for diaphragm 20. Under such circumstances one of body portions 1 should be rotated 180 degrees so that extensions 14 extend from the same side of the sterile connector. This is done so that when diaphragms 20' are simultaneously withdrawn, the sliding action of diaphragms 20' will be such that they will tend to hold end portions 15 in contact with the surface of washers 16 rather than tending to pull one of them up as might occur if one of body portions 1 were not rotated 180 degrees.

While conduits or tubes have not been shown connected to nipples 3 in any of the drawings, it should be appreciated that a conduit or tubing is normally attached to a nipple 3. Once the sterile connection has been made between body portions 1, blood or other fluid can flow in a sterile fashion between body portions 1 and their associated tubings. The sterile connector described hereinabove is intended to have a single use and is intended to be disposable.

In all the foregoing description, body portions 1 have been described as having a circular configuration. This configuration was chosen as a convenience only since other cross-sectional configurations can be utilized without departing from the spirit of the present invention.

Having thus described my invention, what I claim as new, and desire to secure by Letters Patent is:

1. A sterile connector comprising:
   a resilient, deformable washer having an aperture and a passage therein,
   a continuous, removable, yieldable strip material a portion of which is removably adhered to said washer and overlies said aperture, another portion thereof extending through said passage,
   means surrounding said another portion of said strip connected to said passage for receiving said a portion of said strip material when a force is applied to said means and said another portion to expose said aperture.

2. A sterile connector according to claim 1 wherein said means for receiving is a flexible sleeve closed at one end conformal with said strip of material.

3. A sterile connector according to claim 1 further including a diaphragm a portion of which is removably adhered to said washer and overlies said a portion of said strip material and said passage and another portion of which extends beyond the periphery of said washer.

4. A sterile connector according to claim 1 further including a rigid body portion in which said washer, said means for receiving and said strip material are receivable.

5. A sterile connector according to claim 1 wherein said a portion has a U-shaped configuration.

6. A sterile connector according to claim 3 further including a rigid body portion in which said washer, said means for receiving, said strip material and said diaphragm are receivable.

7. A sterile connector according to claim 3 wherein said diaphragm is a continuous, removable, yieldable strip material.

8. A sterile connector according to claim 3 wherein said diaphragm is a continuous, removable, yieldable strip material having a U-shaped configuration.

9. A sterile connector according to claim 4 wherein said rigid body portion includes at least a pair of tangs extending from said rigid body portion and a pair of slots disposed on the periphery of said body portion into which tangs from a mating body portion are receivable.

10. A sterile connector according to claim 4 further including an aperture in said rigid body portion disposed in registry with said aperture in said washer.

11. A sterile connector according to claim 4 further including a channel in said rigid body portion into which said means for receiving and said strip material are receivable.

12. A sterile connector according to claim 6 wherein said rigid body portion includes at least a pair of tangs extending from said rigid body portion and a pair of slots disposed on the periphery of said body portion into which tangs from a mating body portion are receivable.

13. A sterile connector according to claim 6 further including an aperture in said rigid body portion disposed in registry with said aperture in said washer.

14. A sterile connector according to claim 6 further including a channel in said rigid body portion into which said means for receiving and said strip material are receivable.

15. A sterile connector comprising a resilient, deformable washer having an aperture therein,
    a flexible tab removably adhered to said washer and disposed in overlying relationship with said aperture, and, means connected to said washer for receiving said tab when a force is applied to said tab to expose said aperture.

16. A sterile connector according to claim 15 wherein said means into which said tab is receivable includes a flexible sleeve closed at at least one end said sleeve being conformal with said tab.

17. A sterile connector according to claim 15 further including a diaphragm a portion of which is removably adhered to said washer and overlies a portion of said tab and another portion of which extends beyond the periphery of said washer.

18. A sterile connector according to claim 15 further including a rigid body portion in which said washer, said means into which said tab is receivable and said tab are receivable.

19. A sterile connector according to claim 15 wherein said flexible tab includes a portion having a U-shaped configuration.

20. A sterile connector according to claim 15 wherein said flexible tab has a free-end portion disposed within said means into which said tab is receivable.

21. A sterile connector according to claim 17 further including a rigid body portion in which said washer, said means into which said tab is receivable, said tab and said diaphragm are receivable.

22. A sterile connector according to claim 17 wherein said diaphragm in a continuous, removable, yieldable strip material.

23. A sterile connector according to claim 17 wherein said diaphragm is a continuous, removable, yieldable strip material having a U-shaped configuration.

24. A sterile connector according to claim 18 wherein said rigid body portion includes at least a pair of tangs extending from said rigid body portion and a pair of slots disposed on the periphery of said body portion into which tangs from a mating body portion are receivable.

25. A sterile connector according to claim 18 further including an aperture in said rigid body portion disposed in registry with said aperture in said washer.

26. A sterile connector according to claim 18 further including a channel in said rigid body portion into which said means into which said tab is receivable and said tab are receivable.

27. A sterile connector according to claim 21 wherein said rigid body portion includes at least a pair of tangs extending from said rigid body portion and a pair of slots disposed on the periphery of said body portion into which tangs from a mating body portion are receivable.

28. A sterile connector according to claim 21 further including an aperture in said rigid body portion disposed in registry with said aperture in said washer.

29. A sterile connector according to claim 21 further including a channel in said rigid body portion into which said means into which said tab is receivable and said tab are receivable.

* * * * *